(12) United States Patent
Ostendorf

(10) Patent No.: US 9,464,108 B2
(45) Date of Patent: Oct. 11, 2016

(54) COMBINED SYNTHESIS ROUTE FOR DESOGESTREL AND ETONOGESTREL

(71) Applicant: MSD Oss B.V., Oss (NL)

(72) Inventor: Martin Ostendorf, Oss (NL)

(73) Assignee: Merck Sharp & Dohme B.V., Haarlem (NL)

( * ) Notice: Subject to any disclaimer, the term of this patent is extended or adjusted under 35 U.S.C. 154(b) by 116 days.

(21) Appl. No.: 14/383,709

(22) PCT Filed: Mar. 13, 2013

(86) PCT No.: PCT/EP2013/055084
§ 371 (c)(1),
(2) Date: Sep. 8, 2014

(87) PCT Pub. No.: WO2013/135744
PCT Pub. Date: Sep. 19, 2013

(65) Prior Publication Data
US 2015/0031875 A1 Jan. 29, 2015

(30) Foreign Application Priority Data
Mar. 15, 2012 (EP) ..................... 12159747

(51) Int. Cl.
| | | |
|---|---|---|
| C07J 31/00 | (2006.01) | |
| C07J 21/00 | (2006.01) | |
| C07J 33/00 | (2006.01) | |
| C07J 1/00 | (2006.01) | |
| C07J 11/00 | (2006.01) | |

(52) U.S. Cl.
CPC ............. *C07J 33/007* (2013.01); *C07J 1/0059* (2013.01); *C07J 1/0096* (2013.01); *C07J 11/00* (2013.01); *C07J 21/008* (2013.01)

(58) Field of Classification Search
CPC ....................................................... C07J 33/007
USPC ................................................ 552/524; 540/7
See application file for complete search history.

(56) References Cited

U.S. PATENT DOCUMENTS

| 3,927,046 A | 12/1975 | van den Broek |
| 4,031,074 A | 6/1977 | deJongh et al. |
| 2005/0234251 A1 | 10/2005 | Grisenti et al. |

FOREIGN PATENT DOCUMENTS

| CN | 1865276 A | 11/2006 |
| CN | 101857624 A | 10/2010 |

OTHER PUBLICATIONS

4th Edition, Oxidation or Dehydrogenation of Alcohols to Aldehydes and Ketones, Organic Chemisry, 1992, pp. 1167-1171.
4th Edition, The Peterson Olefination Reaction, March J. Advanced Organic Chemistry,—, pp. 952-953,
Cairns, J. et al., Rapid, Efficient Regeneration of Steroidal Ketones from Thioacetals by Periodic Acid, J. Chem. Soc., Chem. Commun, 1980, p. 886-887, vol. 18.
Dess, et al, Readily Accessible 12-I-5 Oxidant for the Conversion of Primary and Secondary Alcohols to Aldehydes and Ketones, J. Org. Chem, 1983, pp. 4155-4156, vol. 48.
Gao, H. et al., Synthesis of 13-Ethyl-11-Methylene-18,19-DINOR-17a-PREGN-4-EN-20-YN-17-OL, OPPI Briefs, 1997, p. 572-576, vol. 29, No. 5.
Greene, et al., Protection for the Carbonyl Group, Organic Synthesis, 1999, pp. 312-344.
Krishnaveni, N. S. et al., Mild and Efficient Hydrolysis of Aromatic Thioacetals/Thioketals using o-Iodoxybenzoic acid (IBX) in Presence of B-Cyclocextrin in Water, Synthesis, 2003, p. 2295.
Ley, S. V. et al., Tetrapropylammonium Perruthenate, Pr4N+RuO-4, TPAP: A Catalytic Oxidant for Organic Synthesis, Synthesis, 1994, p. 639.
Tebbe, et al., Olefin Homologation with Titanium Methylene Compounds, J. Am. Chem. Soc, 1978, p. 3611-3613, vol. 100.
Van Den Heuvel, M. J., et al, A partial synthesis of 13-ethyl-11-methylene-18,19-dinor-17a-pregn-4-en-20-yn-17-ol (desogestrel) based upon intramolecular oxidation of an 11B-hydroxy-19-norsteroid to the 18 11B-lactone, Requeil des Travaux Chimiques des Pays-Bas, 1988, p. 331-334, vol. 107.

*Primary Examiner* — Barbara P Badio
(74) *Attorney, Agent, or Firm* — Janet E. Fair; Anna L. Cocuzzo

(57) ABSTRACT

The present invention relates to a synthesis route and to steroid derivatives of general formula VI and VII useful in the synthesis of desogestrel and etonogestrel.

(I)

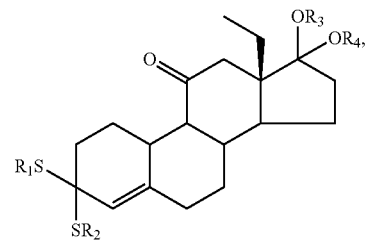

(II)

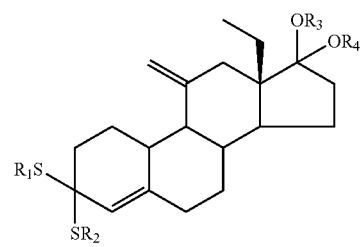

11 Claims, No Drawings

COMBINED SYNTHESIS ROUTE FOR DESOGESTREL AND ETONOGESTREL

CROSS-REFERENCE TO RELATED APPLICATIONS

This application is a U.S. National Phase application under 35 U.S.C. §371 of PCT Application No. PCT/EP2013/055084, filed Mar. 13, 2013, which published as WO 2013/135744 A1 on Sep. 19, 2013, and claims priority under 35 U.S.C. §365(b) from European Application No. EP12159747.0, filed Mar. 15, 2012.

The present invention relates to a process for the synthesis of desogestrel and etonogestrel. The present invention further relates to intermediates used in said process.

Desogestrel (13β-ethyl-17β-hydroxy-11-methylene-18, 19-dinor-17α-pregn-4-en-20-yn) is a molecule used in hormonal contraceptives. Etonogestrel (3-oxodesogestrel or 13β-ethyl-17-hydroxy-11-methylene-18,19-dinor-17α-pregn-4-en-20-yn-3-one) is the active metabolite of desogestrel. It is a molecule used in hormonal contraceptives, most notably the subdermal implant IMPLANON® (etonogestrel implant) and the contraceptive vaginal ring NUVARING® (etonogestrel/ethinyl estradiol vaginal ring).

Etonogestrel is known, for example, from U.S. Pat. No. 3,927,046 A. It can be synthesized according to methods described in U.S. Pat. No. 4,031,074 A or HEUVEL, M. J., et al. *Requeil des Travaux Chimiques des Pays-Bas*. 1988, vol. 107, no. 4, p. 331-334. The key step in this synthesis is the oxidation of the 18 methyl group to give a lactone which is subsequently converted to a 13β-ethyl steroid by a Grignard reaction and a Wolff-Kishner reduction. This process, however, uses a long and therefore labour-intensive route.

Desogestrel and etonogestrel are known, for example from CN 1865276 A. They can, for example, be synthesised according to the method described in CN 1865276 A. This synthesis adopts 13β-ethyl-1,3,5(10),8(9)-estratetraene-17-ol as raw material for the synthesis of desogestrel and etonogestrel. In this method, however, five steps are required for the introduction of the 11-functionality.

US 2005/0234251 A describes the synthesis of desogestrel from 18-methylnordione

Hongwu Gao et al in OPPI BRIEFS, 1997, vol. 29, no. 5, p. 572-576 describe the synthesis of desogestrel from 13β-ethyl-11α-hydroxy-gon-4-ene-3,17-dione (1). As part of this synthesis, an 11-ketone 2 was obtained by oxidation of 1 and converted, by treatment with ethylene glycol/triethyl orthoformate/p-toluenesulfonic acid in methylene chloride at reflux temperature, into the 3,17-bisethylene acetal 3. This process, however, is disadvantageous in that selective protection of two of the carbonyl groups of the triketone 2 is required.

Scheme 1 Synthesis method according to Gao et al.

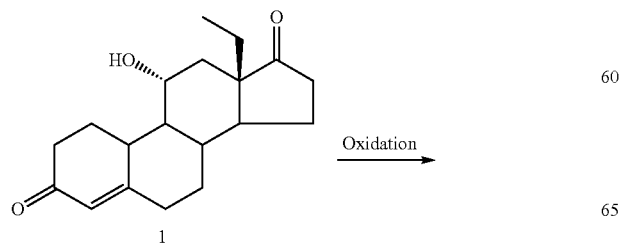

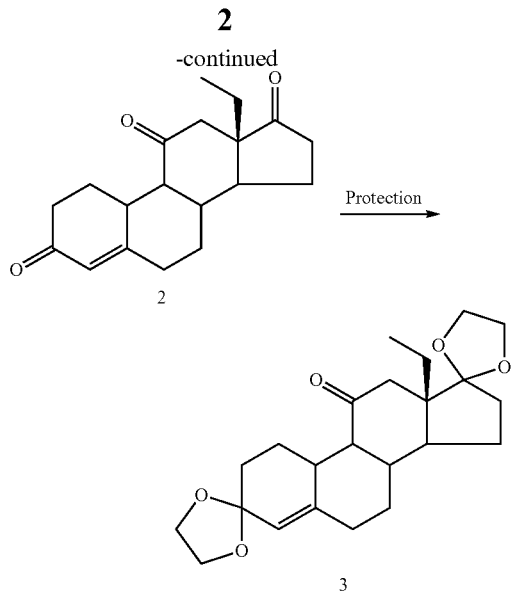

As desogestrel and etonogestrel are used in hormonal contraceptives, there remains a need for alternative synthesis routes that are efficient and cost-effective.

In a first aspect the present invention relates to a process for the manufacture of a steroid derivative according to formula IX

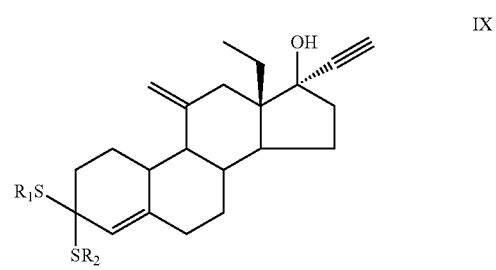

using a steroid derivative of general formula VI or VII

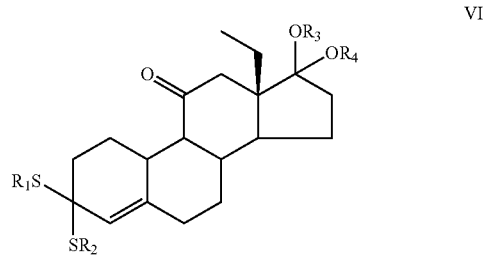

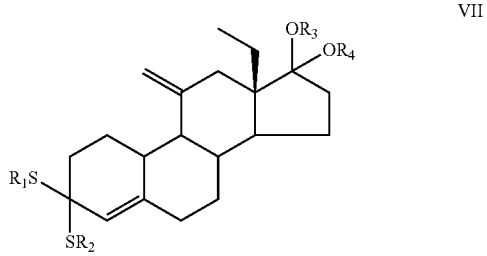

wherein in the steroid derivatives of general formula VI, VII and IX, $R_1$ and $R_2$ are the same and are selected from H and (1-4C)alkyl; or R₁ and R₂, together with the sulphur atoms to which they are attached, form a 1,3-dithiolane or 1,3-dithiane, said dithiolane or dithiane being optionally substituted with one or more (1-4C)alkyl group; and R₃ and R₄ are the same and are selected from H and (1-4C)alkyl; or R₃ and R₄, together with the oxygen atoms to which they are attached, form a 1,3-dioxolane or 1,3-dioxane, said dioxolane or dioxane being optionally substituted with one or more (1-4C)alkyl group.

In another aspect, the present invention relates to a process for the manufacture of a steroid derivative of general formula IX, comprising steps 1 through to 6 according to Scheme 2:

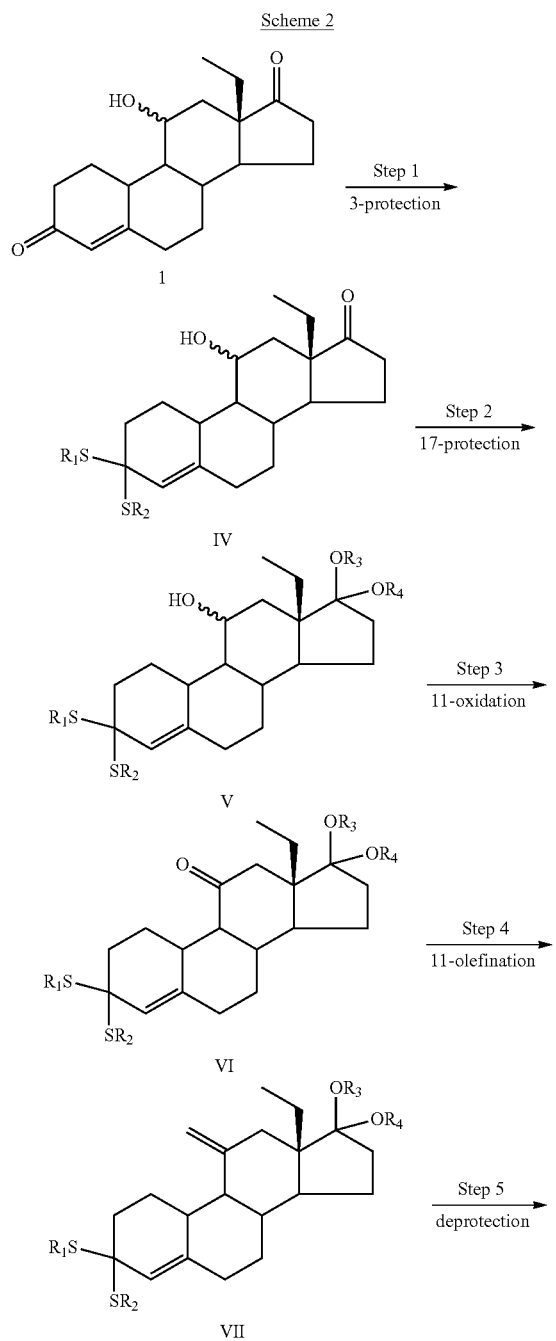

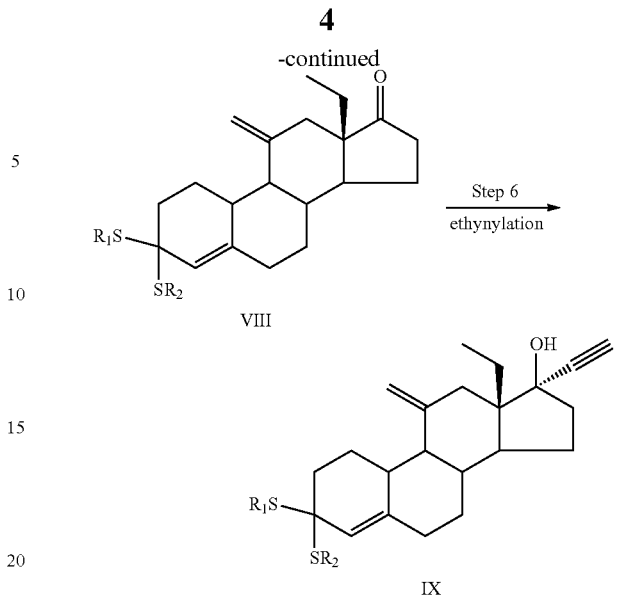

In this process, in the steroid derivatives of general formula IV, V, VI, VII, VIII and IX, $R_1$ and $R_2$ are the same and are selected from H and (1-4C)alkyl; or $R_1$ and $R_2$, together with the sulphur atoms to which they are attached, form a 1,3-dithiolane or 1,3-dithiane, said dithiolane or dithiane being optionally substituted with one or more (1-4C)alkyl group and in the steroid derivatives of general formula V, VI and VII, $R_3$ and $R_4$ are the same and are selected from H and (1-4C)alkyl; or $R_3$ and $R_4$, together with the oxygen atoms to which they are attached, form a 1,3-dioxolane or 1,3-dioxane, said dioxolane or dioxane being optionally substituted with one or more (1-4C)alkyl group.

In step 1, 13β-ethyl-11-hydroxygon-4-ene-3,17-dione, (1) is reacted with a thioalcohol into a 3-dithioacetal steroid derivative of general formula IV. Such dithioacetalisation reactions are known in the art, for example, from Protective groups in Organic Synthesis, Greene, T. W.; Wuts, P. G. 3th edition 1999, pages 333-344.

In step 2, the 3-dithioacetal steroid derivative of general formula IV is reacted with an alcohol or a diol to protect the 17-keto group to obtain a 17-acetal-3-dithioacetal steroid derivative of general formula V. Acetalisation reactions are known, for example from Protective groups in Organic Synthesis Greene, T. W.; Wuts, P. G. 3th edition 1999, pages 312-322.

In step 3, the 11-hydroxy group in the 17-acetal-3-dithioacetal steroid derivative of general formula V is oxidized to obtain a 11-keto-17-acetal-3-dithioacetal steroid derivative of general formula VI. Examples of oxidising agents which can be used include: pyridinium dichromate (see Advanced Organic Chemistry March, J. 4th edition 1992, pages 1167-1171); N-methylmorpholine-N-oxide (NMO) in combination with tetrapropylammonium perruthenate (TPAP), (for TPAP, see a catalytic oxidant for Organic Synthesis, Ley, S. V.; Norman, J.; Griffith W. P.; Marsden, S. P., *Synthesis* 1994, 639) or the so-called Dess-Martin periodinane reagent, (see Readily accessible 12-I-5 oxidant for the conversion of primary and secondary alcohols to aldehydes and ketones Dess, D. B.; Martin, J. C., *J. Org. Chem.* 1983, 48: 4155).

In step 4, the 11-keto-17-acetal-3-thioacetal steroid derivative of general formula VI is methylenylated to give a 11-methylene-17-acetal-3-dithioacetal steroid derivative of general formula VII (i.e., the 11-keto is converted into a 11-methylene). Such olefination reactions are well known in the art. Examples include the Peterson olefination reaction (see March J, Advanced Organic Chemistry, 4$^{th}$ Edition, pages 952-953); the Wittig reaction (see March J, Advanced Organic Chemistry, 4$^{th}$ Edition, pages 956-963); the Horner-Wadsworth-Emmons reaction (see March J, Advanced Organic Chemistry, 4$^{th}$ Edition, pages 958-960) or the Tebbe olefination (see F. N. Tebbe, G. W. Parshall and G. S. Reddy, J. Am. Chem. Soc., 1978, 100, 3611-3613).

In step 5, the 11-methylene-17-acetal-3-dithioacetal steroid derivative of general formula VII is hydrolysed to obtain a 11-methylene 3-dithioacetal steroid derivative of general formula VIII, (i.e., the acetal protecting group at the 17-position in the 11-methylene 3-dithioacetal derivative of general formula VII is hydrolysed. Such hydrolytic deprotection reactions are well known in the art (for examples, see Protective groups in Organic Synthesis, Greene, T. W.; Wuts, P. G. 3th edition 1999, pages 312-322).

In step 6, the 11-methylene 3-dithioacetal steroid derivative of general formula VIII is ethynylated to give a 20-yn-11-methylene-3-dithioacetal steroid derivative of general formula IX (i.e., the 17 keto is reacted with acetylene).

The 20-yn-11-methylene-3-dithioacetal steroid derivative of general formula IX serves as a precursor for the synthesis of etonogestrel or desogestrel.

In a further apect, etonogestrel is obtained from the 20-yn-11-methylene-3-dithioacetal steroid derivative of general formula IX by deprotection of the 3-dithioacetal as shown in Scheme 3 (step 7).

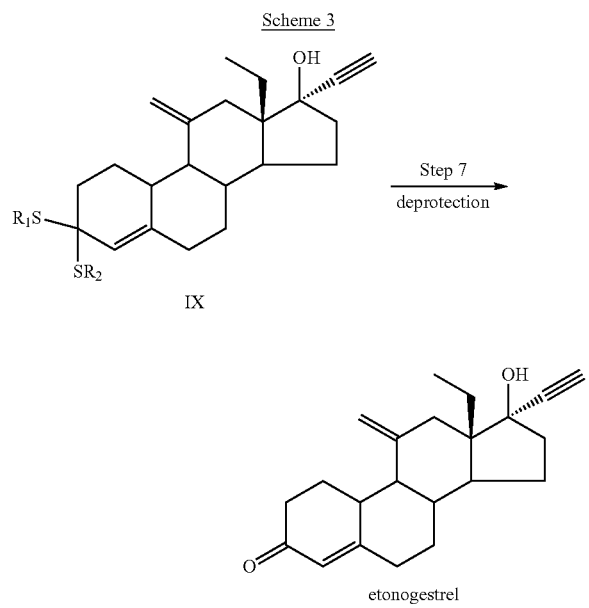

Scheme 3 etonogestrel

This may be effected using acid, for example, using periodic acid (see Cairns J. and Logan R. T., J. Chem. Soc., Chem. Commun., 1980, 18, 886-887). Alternatively, the dithioacetal is removed using thallium nitrate (TTN) (see Protective groups in Organic Synthesis, Greene, T. W.; Wuts, P. G. 3th edition 1999, pages 333-344). The deprotection may also be effected using stabilised 2-iodobenzoic acid (SIBX) and β-cyclodextrin (β-CD)—see N. Srilakshmi Krishnaveni, K. Surendra, Y. V. D. Nageswar and K. Rama Rao, Synthesis 2003, 2295.

In a further aspect, desogestrel is obtained from the 20-yn-11-methylene-3-dithioacetal steroid derivative of general formula IX by deprotection of the 3-dithioactetal followed by reduction of the resulting carbonyl group as shown in Scheme 4 (step 8).

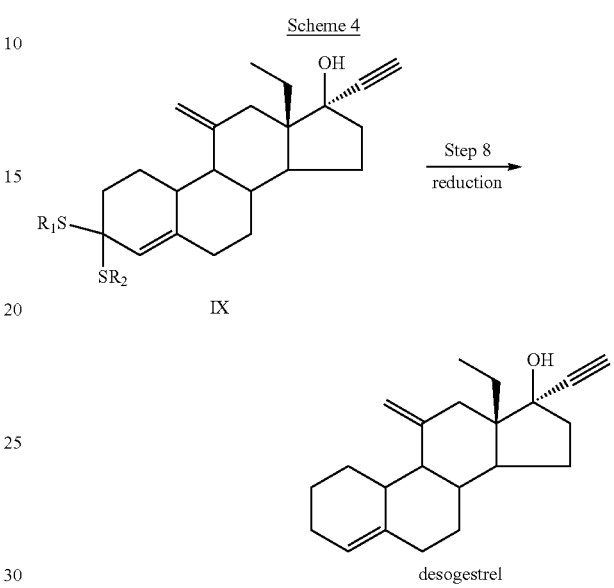

Scheme 4 desogestrel

In a further embodiment of the present invention is the process according to Scheme 2 comprising steps 1, 2 and 3.

In a further embodiment of the present invention is the process according to Scheme 2 comprising steps 1, 2, 3 and 4.

In a further embodiment of the present invention is the process according to Scheme 2 comprising steps 4, 5 and 6.

In a further embodiment of the present invention is the process according to Scheme 2 comprising steps 5 and 6.

In a further embodiment of the present invention, the process of scheme 2 employs the 11α- or 11β-epimer of starting material (1), i.e., 13β-ethyl-11α-hydroxygon-4-ene-3,17-dione or 13β-ethyl-11β-hydroxygon-4-ene-3,17-dione or a diastereomeric mixture thereof.

In a further embodiment of the present invention, the process of Scheme 2 employs steroid derivatives of general formulae VI, VII, VIII and IX wherein R$_1$ and R$_2$ together with the sulphur atoms to which they are attached form a 1,3-dithiolane or 1,3-dithiane, said dithiolane or dithiane being optionally substituted with one or more (1-4C)alkyl groups. In a further embodiment, R$_1$ and R$_2$ together with the sulphur atoms to which they are attached form a 1,3-dithiolane or 1,3-dithiane. The skilled person will appreciate that in order to form the steroid derivatives of general formulae VI, VII, VIII and IX wherein R$_1$ and R$_2$ together with the sulphur atoms to which they are attached form a 1,3-dithiolane or 1,3-dithiane, in step 1 of the process of scheme 2,13β-ethyl-11-hydroxygon-4-ene-3,17-dione (1) is protected with ethane-1,2-dithiol or propane 1,3-dithiol respectively.

In a further embodiment, in step 1 of the process of Scheme 2,13β-ethyl-11-hydroxygon-4-ene-3,17-dione (1) is reacted with ethane-1,2-dithiol or propane 1,3-dithiol under acidic conditions.

In a further embodiment of the present invention, the process of Scheme 2 employs steroid derivatives of general formulae V, VI and VII wherein $R_3$ and $R_4$ together with the oxygen atoms to which they are attached form a 1,3-dioxolane or 1,3-dioxane, said dioxolane or dioxane being optionally substituted with one or more (1-4C)alkyl groups. In a further embodiment, $R_3$ and $R_4$ together with the oxygen atoms to which they are attached form a 1,3-dioxolane or 1,3-dioxane. The skilled person will appreciate that in order to form the steroid derivatives of general formulae V, VI and VII wherein $R_3$ and $R_4$ together with the oxygen atoms to which they are attached form a 1,3-dioxolane or 1,3-dioxane, in step 2 of the process of scheme 2, the 3-dithioacetal steroid derivative of general formula IV is reacted with ethylene glycol or propylene glycol respectively under acidic conditions.

In a further embodiment of the present invention, in step 3 of the process of scheme 2, the 11-hydroxy group in the 17-acetal,-3-dithioacetal steroid derivative of general formula V is oxidised using pyridinium dichromate.

In a further embodiment of the present invention, in step 3 of the process of scheme 2, the 11-hydroxy group in the 17-acetal,-3-dithioacetal steroid derivative of general formula V is oxidised using N-methylmorpholine-N-oxide (NMO) together with tetrapropylammonium perruthenate (TPAP).

In a further embodiment of the present invention, in step 3 of the process of scheme 2, the 11-hydroxy group in the 17-acetal,-3-dithioacetal steroid derivative of general formula V is oxidised using the Dess-Martin periodinane reagent.

In a further embodiment of the present invention, in step 4 of the process of Scheme 2, the 11-keto group is converted into a methylene group using Peterson reaction conditions. In a further embodiment, in step 4 of the process of scheme 2, the 11-keto group is converted into a methylene group using Peterson reaction conditions and the 11-methylene 17-acetal, 3-dithioacetal steroid derivative of general formula VII is reacted without isolation.

In a further embodiment of the present invention, in step 4 of the process of Scheme 2, the 11-keto group is converted into a 11-methylene group using Wittig reaction conditions.

In a further embodiment of the present invention, in step 4 of the process of Scheme 2, the 11-keto group is converted into a 11-methylene group using the Homer-Wadsworth-Emmons reaction.

In a further embodiment of the present invention, in step 4 of the process of Scheme 2, the 11-keto group is converted into a 11-methylene group using the Tebbe olefination reaction.

In a further embodiment of the present invention, in step 5 of the process of Scheme 2, the 11-methylene-17-acetal-3-dithioacetal steroid derivative of general formula VII is hydrolysed to obtain a 11-methylene 3-dithioacetal steroid derivative of general formula VIII using acid. In a further embodiment, a protic acid is used. In a still further embodiment, hydrochloric acid is used.

In a further embodiment of the present invention, in the process of scheme 2, the 11-keto-17-acetal-3-thioacetal steroid derivative of general formula VI is converted to the 11-methylene 3-dithioacetal steroid derivative of general formula VIII without isolation of the intermediate 11-methylene-17-acetal-3-dithioacetal steroid derivative of general formula VII, i.e., steps 4 and 5 of the process of scheme 2 are combined without isolation of the intermediate product.

In a further embodiment of the present invention, the 20-yn-11-methylene-3-dithioacetal steroid derivative of general formula IX is obtained upon reaction of the precursor 11-methylene 3-dithioacetal steroid derivative of general formula VIII with acetylene. In a further embodiment, the reaction with acetylene is performed under basic conditions.

In a further embodiment of the present invention, in step 7 (Scheme 3), etonogestrel is obtained from the 20-yn-11-methylene-3-dithioacetal steroid derivative of general formula IX by deprotection of the 3-dithioactetal using acid. In a further embodiment, periodic acid is used.

In a further embodiment of the present invention, in step 7 (Scheme 3), etonogestrel is obtained from the 20-yn-11-methylene-3-dithioacetal steroid derivative of general formula IX by deprotection of the 3-dithioactetal using thallium nitrate.

In a further embodiment of the present invention, in step 7 (Scheme 3), etonogestrel is obtained from the 20-yn-11-methylene-3-dithioacetal steroid derivative of general formula IX by deprotection of the 3-dithioactetal using stabilized 2-iodobenzoic acid (SIBX) and β-cyclodextrin (β-CD).

In a further embodiment of the present invention, in step 8 (Scheme 4), desogestrel is obtained from the 20-yn-11-methylene-3-dithioacetal stereoid derivative of general formula IX by deprotection of the 3-dithioactetal followed by reduction of the resulting carbonyl group.

In a further embodiment of the present invention, etonogestrel is obtained by the process according to Scheme 2 wherein, in the steroid derivatives of general formulae IV, V, VI, VII, VIII and IX, $R_1$ and $R_2$, together with the sulphur atoms to which they are attached, form a 1,3-dithiolane and in the steroid derivatives of general formulae V, VI and VII, $R_3$ and $R_4$, together with the oxygen atoms to which they are attached, form a 1,3-dioxolane;

in step 3, the 11-hydroxy group in the 17-acetal,-3-dithioacetal steroid derivative of general formula V is oxidised using pyridinium dichromate;

in step 4, the 11-keto-17-acetal-3-dithioacetal steroid derivative of general formula VI is methylenylated using Peterson reaction conditions followed by deprotection of the 17-diacetal (step 5) using hydrochloric acid without isolation of the 11-methylene-17-acetal-3-dithioacetal steroid derivative of general formula VII and in step 7 (Scheme 3), the 3-dithioacetal is deprotected using periodic acid.

In a further embodiment of the present invention, desogestrel is obtained by the process according to Scheme 2 wherein, in the steroid derivatives of general formulae IV, V, VI, VII, VIII and IX, $R_1$ and $R_2$, together with the sulphur atoms to which they are attached, form a 1,3-dithiolane;

in the steroid derivatives of general formulae V, VI and VII, $R_3$ and $R_4$, together with the oxygen atoms to which they are attached, form a 1,3-dioxolane;

in step 3, the 11-hydroxy group in the 17-acetal,-3-dithio-acetal steroid derivative of general formula V is oxidised using pyridinium dichromate;

in step 4, the 11-keto-17-acetal-3-dithioacetal steroid derivative of general formula VI is methylenylated using Peterson reaction conditions followed by deprotection of the 17-diacetal (step 5) using hydrochloric acid without isolation of the 11-methylene-17-acetal-3-dithioacetal steroid derivative of general formula VII and in step 8 (Scheme 4), the 3-dithioacetal is deprotected using periodic acid followed by reduction of the resulting carbonyl group.

In the latter two embodiments etonogestrel and desogestrel are obtained by the process according to scheme 5 proceeding via intermediates 4-8:

Scheme 5

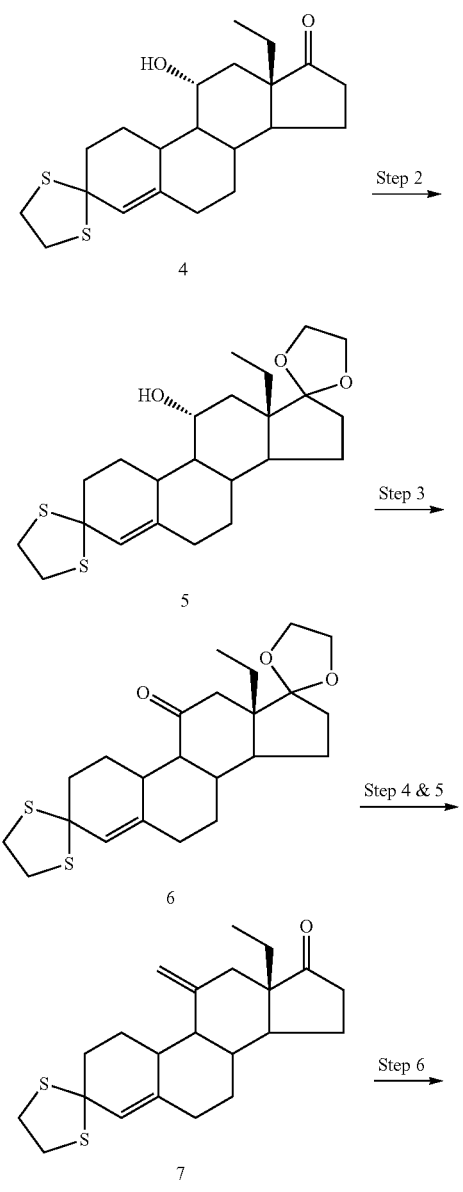

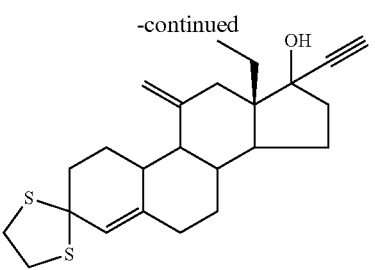

8

Step 8 / \ Step 7

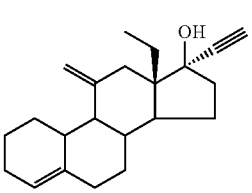

desogestrel

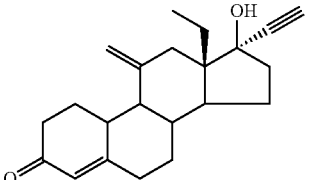

etonogestrel

In a further embodiment of the present invention is a steroid derivative of general formula VI or VII,

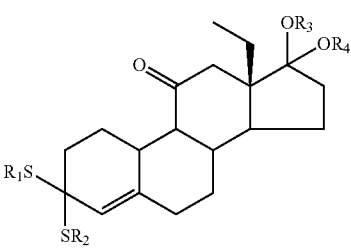

VI

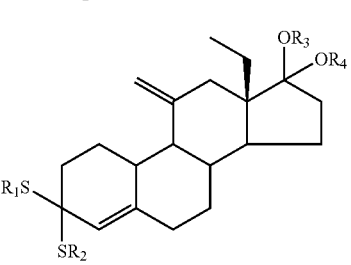

VII wherein, $R_1$ and $R_2$ are the same and are selected from H and (1-4C)alkyl; or $R_1$ and $R_2$, together with the sulphur atoms to which they are attached, form a 1,3-dithiolane or 1,3-dithiane, said dithiolane or dithiane being optionally substituted with one or more (1-4C)alkyl group and $R_3$ and $R_4$ are the same and are selected from H and (1-4C)alkyl; or $R_3$ and $R_4$, together with the oxygen atoms to which they are attached, form a 1,3-dioxolane or 1,3-dioxane, said dioxolane or dioxane being optionally substituted with one or more (1-4C)alkyl group.

In a further embodiment of the present invention is a steroid derivative selected from:
13β-ethyl-cyclic-3-(1,2-ethanediyl dithioacetal)-cyclic-17-(1,2-ethanediyl acetal)-gon-4-ene-3,11,17-trione (6) and
13β-ethyl-11-methylene-cyclic-3-(1,2-ethanediyl dithioacetal)-cyclic-17-(1,2-ethanediyl acetal)-gon-4-ene-3,17-dione (7).

The term (1-4C)alkyl, as used herein, represents a branched or unbranched alkyl group having 1-4 carbon atoms. Examples of such groups are methyl, ethyl, isopropyl and tertiary butyl.

The steroid derivatives of the present invention may also exist as amorphous forms. Multiple crystalline forms are also possible. All these physical forms are included within the scope of the present invention.

The steroid derivatives of the present invention may also form solvates such as hydrates. "Solvate" means a physical association of a steroid derivative according to the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolable solvates. Non-limiting examples of suitable solvates include ethanolates, methanolates, and the like. "Hydrate" is a solvate wherein the solvent molecule is $H_2O$.

Preparation of solvates is generally known. Thus, for example, M. Caira et al, *J. Pharmaceutical Sci.*, 93(3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS PharmSciTech.*, 5(1), article 12 (2004); and A. L. Bingham et al, *Chem. Commun.*, 603-604 (2001). A typical, non-limiting, process involves dissolving the steroid derivative according to the present invention in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

The present invention also embraces isotopically-labelled compounds of the steroid derivatives described and claimed herein which are identical to those recited herein, but for the fact that one or more atoms are replaced by an atom having an atomic mass or mass number different from the atomic mass or mass number usually found in nature. Examples of isotopes that can be incorporated into steroid derivatives of the invention include isotopes of hydrogen, carbon, nitrogen, oxygen and sulphur such as $^2H$, $^3H$, $^{11}C$ $^{13}C$, $^{14}C$, $^{15}N$, $^{18}O$, $^{17}O$ and $^{35}S$ respectively.

Certain isotopically-labelled compounds of Formula I (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Certain isotopically labeled compounds of formula (I) can be useful for medical imaging purposes, e.g., those labeled with positron-emitting isotopes, like $^{11}C$ or can be useful for application in Positron Emission Tomography (PET) and those labeled with gamma ray emitting isotopes, can be userful for application in single photon emission computed tomography (SPECT). Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

The present invention also relates to those processes or products, wherein all specific conditions of the various embodiments of the invention, as described here above, occur in any combination within the definition of the process according to Scheme 2

EXAMPLES

The invention is illustrated by the following non-limitative examples.

11α-hydroxy-18-methylnordione (1) was purchased from the Chinese company Beijing KeYiFeng Biotech. Development Co. Ltd.

Example 1

13β-Ethyl-11α-hydroxy-,cyclic 3-(1,2-ethanediyl dithioacetal)gon-4-ene-3,17-dione, (4)

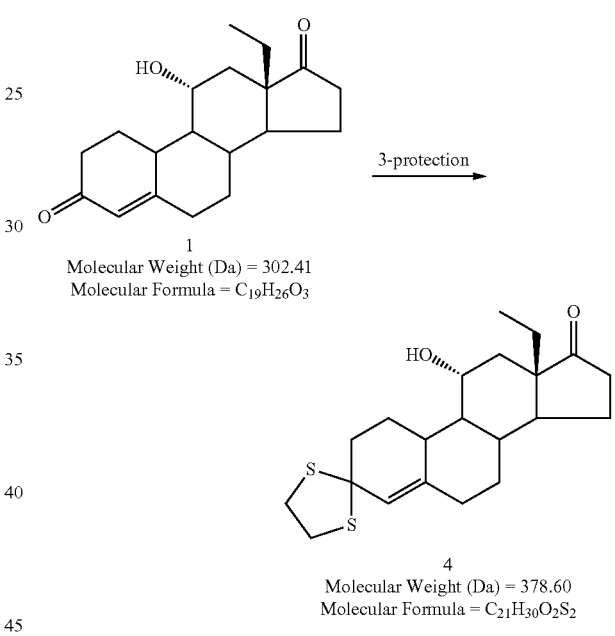

A suspension of (1) (162 g, 536 mmol), p-toluenesulfonic acid (8.4 g, 22 mmol) and 1,2-ethanedithiol (65.4 g, 691 mmol) in methanol (960 mL) was refluxed for 20 min. The product was precipitated by the addition of water (250 mL). After cooling to 30° C. and an additional agitation time of 2 h, the solid was filtered off and washed with a 5:1 methanol/water mixture (160 mL). The solid was then washed with a NaOH solution (140 mL MeOH, 5 mL water, 21 mL 33% aqueous NaOH) at 30° C. Finally, the solid was washed with water until a neutral pH. The wet crystal cake was suspended in acetone (800 mL) and dichloromethane (800 mL). After concentration to a volume of 500 mL under atmospheric pressure, crystals were obtained. These were isolated by filtration and washed with acetone. The product (4) was dried at 70° C. in vacuo. Product yield (yellow crystals): 146 g (386 mmol, 72%). $^1H$ NMR (600 MHz, $CDCl_3$): 0.85 (t, 3 H, C18$H_2$C$H_3$), 0.92 (m, 1 H, C9H), 1.06 (m, 1 H, C7HH), 1.08 (m, 1 H, C12HH), 1.20 (m, 1 H, C11HOH), 1.35 (m, 1 H, C18HHC$H_3$), 1.45 (m, 1 H, C18HHC$H_3$), 1.46 (m, 1 H, C8H), 1.46 (m, 1 H, C14H), 1.61 (m, 1 H, C15HH), 1.82 (m, 1 H, C7HH), 1.92 (m, 1 H, C15HH), 1.97 (m, 1 H, C1HH), 2.01 (m, 1 H, C2HH), 2.01 (m, 1 H, C10H), 2.07 (m, 1 H, C6HH), 2.13 (m, 1 H, C16HH), 2.24 (m, 1 H, C2HH), 2.34 (m, 1 H, C1HH), 2.36 (m, 1 H, C12HH), 2.44 (m, 1 H, C16HH), 2.31 (m, 1 H, C6HH), 3.27 (m, 2 H, SCH$_2$CH$_2$S), 3.36 (m, 2 H, SCH$_2$CH$_2$S), 3.76 (m, 1 H, C11HOH), 5.64 (s, 1 H, C4H). $^{13}$C NMR (150 MHz, CDCl$_3$): 7.6 (C18H$_2$CH$_3$), 18.7 (C18H$_2$CH$_3$), 21.1 (C15), 29.0 (C1), 30.5 (C7), 35.3 (C6), 35.8 (C16), 38.6 (C12), 39.1 (C8), 39.7 and 39.8 (SCH$_2$CH$_2$S), 40.2 (C2), 42.2 (C10), 50.1 (C14), 51.3 (C13), 55.3 (C9), 65.5 (C3), 71.9 (C11), 126.3 (C4), 141.3 (C5), 217.9 (C17). MS (ESI) observed ions 379.2 (M+H)$^+$, 401.2 (M+Na)$^+$, 417.1 (M+K)$^+$, 779.3 (2M+Na)$^+$, 795.3 (2M+K)$^+$.

Example 2

13β-ethyl-11α-hydroxy-,cyclic-17-(1,2-ethanediyl acetal),cyclic 3-(1,2-ethanediyl dithioacetal)gon-4-ene-3,17-dione, (5)

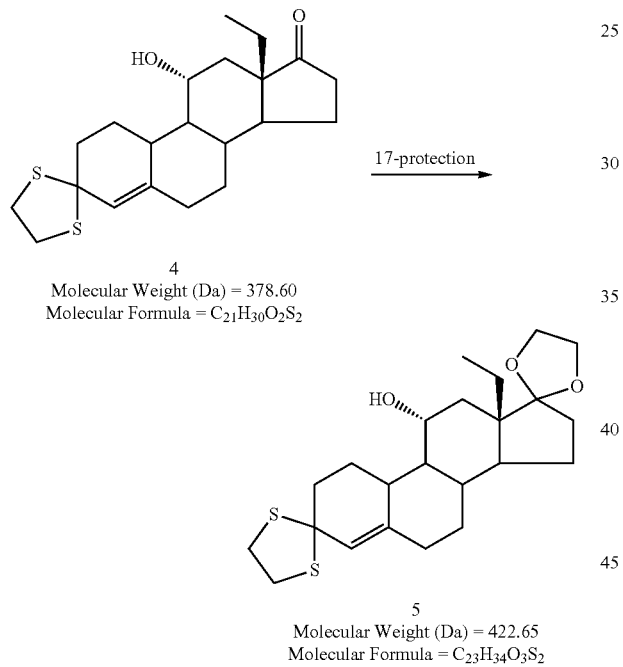

A solution of steroid (4) (2.7 kg, 7.13 mol), ethylene glycol (6.3 kg, 102 mol), triethyl orthoformate (5.1 kg, 34.3 mol) and p-toluenesulfonic acid (175 g, 1.0 mol) in methylene chloride (22 L) was reacted for 7 h at 40° C. and 13 h at 20° C. The reaction was quenched by the addition of pyridine (400 mL, 4.9 mol) and water (27 L). The layers were separated and the water layer was extracted with methylene chloride (3 L). This methylene chloride portion was combined with the main organic layer. The combined organic layers were twice washed with water (6 L, 1% pyridine). The combined organic layer was concentrated under atmospheric pressure to a volume of 6 L. After the addition of methanol (40 L) and pyridine (100 mL), the solution was concentrated under atmospheric pressure to a volume of 13 L. The product thus obtained in solution was added to water (34 L) at a temperature of 5° C. The obtained solid was isolated by filtration. The product was twice washed with water (3 L). Product (5) yield (off-white crystals): 2.89 kg (6.84 mol, 96%). $^1$H NMR (600 MHz, CDCl$_3$): 0.86 (q, 1 H, C9H), 1.00 (m, 1 H, C7HH), 1.04 (t, 3 H, C18H$_2$CH$_3$) 1.07 (m, 1 H, C11HOH), 1.21 (m, 1 H, C15HH), 1.30 (m, 1 H, C8H), 1.35 (m, 2 H, C18H$_2$CH$_3$), 1.45 (m, 1 H, C12HH), 1.58 (m, 1 H, C14H), 1.63 (m, 1 H, C15HH), 1.71 (m, 1 H, C7HH), 1.82 (m, 1 H, C16HH),1.96 (m, 1 H, C1HH), 1.99 (m, 1 H, C10H), 2.00 (m, 1 H, C12HH), 2.02 (m, 1 H, C6HH), 2.03 (m, 1 H, C2HH), 2.09 (m, 1 H, C16HH), 2.26 (m, 1 H, C2HH), 2.26 (m, 1 H, C6HH), 2.38 (m, 1 H, C1HH), 3.26 (m, 2 H, SCH$_2$CH$_2$S), 3.36 (m, 2 H, SCH$_2$CH$_2$S), 3.62 (m, 1 H, C11HOH), 3.85 (m, 2 H, OCH$_2$CH$_2$O), 3.90 (m, 2 H, OCH$_2$CH$_2$O), 5.62 (s, 1 H, C4H). $^{13}$C NMR (150 MHz, CDCl$_3$): 9.1 (C18H$_2$CH$_3$), 20.7 (C18H$_2$CH$_3$), 21.9 (C15), 29.3 (C1), 31.0 (C7), 35.5 (C6), 34.7 (C16), 38.4 (C12), 39.8 (C8), 39.7 and 39.8 (SCH$_2$CH$_2$S), 40.4 (C2), 42.4 (C10), 48.0 (C13), 49.8 (C14), 55.1 (C9), 65.3 and 64.4 (OCH$_2$CH$_2$O), 65.7 (C3), 72.9 (C11), 119.8 (C17), 125.9 (C4), 141.8 (C5). MS (ESI) observed ions 423.2 (M+H)$^+$, 445.2 (M+Na)$^+$, 461.2 (M+K)$^+$, 867.4 (2M+Na)$^+$.

Example 3

13β-ethyl-,cyclic 17-(1,2-ethanediyl acetal),cyclic 3-(1,2-ethanediyl dithioacetal) gon-4-ene-3,11,17-trione (6)

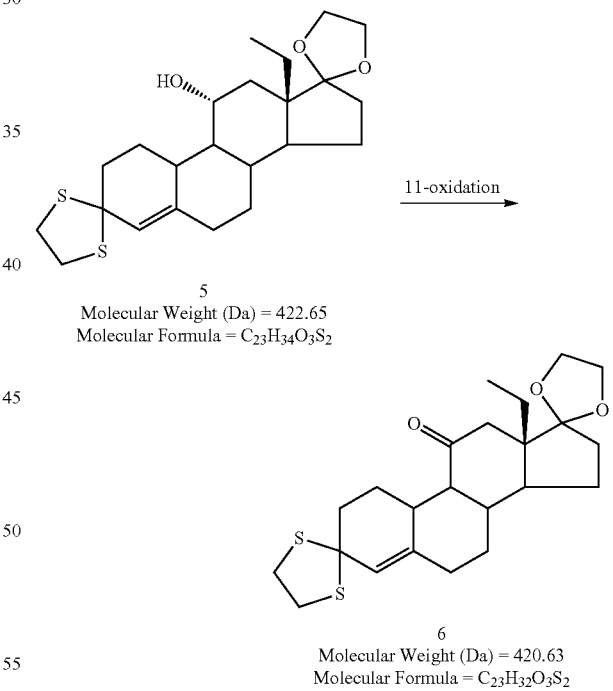

Example 3A

Conversion Using N-methylmorpholine-N-oxide (NMO) and Tetrapropylammonium Perruthenate (TPAP)

A solution of steroid (5) (5.0 g, 11.8 mmol), N-methylmorpholine-N-oxide (NMO, 4.22 g, 36.0 mmol) and tetrapropylammonium perruthenate (TPAP, 0.33 g, 0.92 mmol)

in DCM (100 mL) was stirred for 90 min at room temperature. The reaction was quenched by the addition of tetraethylammonium bromide (7.6 g, 36.0 mmol) and diethyl ether (400 mL). Solids were filtered off and washed with diethyl ether (2×25 mL). The solvents from the filtrate were replaced by methanol (50 mL). The product solution was slowly poured into water (200 mL) in the presence of pyridine (2 mL). The crystals were filtered off and dried at 50° C. in vacuo. Product yield: 2.8 g (6.7 mmol, 56%).

Example 3B

Conversion Using Pyridinium Dichromate

A solution of steroid (5) (5 g, 11.8 mmol) and pyridinium dichromate (9.0 g, 23.9 mmol) in dry DMF (39 mL) was agitated for 2 h at 30° C. The reaction mixture was added to water (200 mL) in 30 min at 30° C. The crystals were filtered off, washed with water and dried in vacuo. Product (6) yield: 4.4 g (10.5 mmol, 89%).

NMR and mass spectrometry data of (6)

$^1$H NMR (600 MHz, CDCl$_3$): 1.04 (t, 3 H, C18H$_2$CH$_3$), 1.12 (m, 1 H, C7HH), 1.21 (m, 1 H, C1HH), 1.21 (m, 1 H, C18HHCH$_3$), 1.34 (m, 1 H, C15HH), 1.44 (m, 1 H, C18HHCH$_3$), 1.58 (m, 1 H, C8H), 1.70 (m, 1 H, C15HH), 1.78 (m, 1 H, C7HH), 1.83 (m, 1 H, C9H), 1.93 (m, 1 H, C16HH), 1.94 (m, 1 H, C6HH), 2.05 (m, 1 H, C2HH), 2.13 (m, 1 H, C16HH), 2.16 (m, 1 H, C14H), 2.19 (m, 1 H, C2HH), 2.25 (m, 1 H, C6HH), 2.28 (m, 1 H, C10H), 2.36 (m, 1 H, C1HH), 2.45 (d, 1 H, C12HH), 2.59 (d, 1 H, C12HH), 3.22 (m, 2 H, SCH$_2$CH$_2$S), 3.35 (m, 2 H, SCH$_2$CH$_2$S), 3.81 (m, 2 H, OCH$_2$CH$_2$O), 3.91 (m, 2 H, OCH$_2$CH$_2$O), 5.65 (s, 1 H, C4H). $^{13}$C NMR (150 MHz, CDCl$_3$): 8.8 (C18H$_2$CH$_3$), 21.6 (C18H$_2$CH$_3$), 21.0 (C15), 28.5 (C1), 31.2 (C7), 34.3 (C6), 34.7 (C10), 34.9 (C16), 39.7 and 40.0 (SCH$_2$CH$_2$S), 40.5 (C2), 41.5 (C8), 45.1 (C12), 51.0 (C14), 52.7 (C13), 60.2 (C9), 65.4 and 64.3 (OCH$_2$CH$_2$O), 65.6 (C3), 118.7 (C17), 127.1 (C4), 140.0 (C5), 212.0 (C11). MS (ESI) observed ions 412/438 (M+H/M+NH$_4$)$^+$.

Example 4

11-methylene-13β-ethyl-,cyclic 3-(1,2-ethanediyl dithioacetal)gon-4-ene-3,17-dione (8)

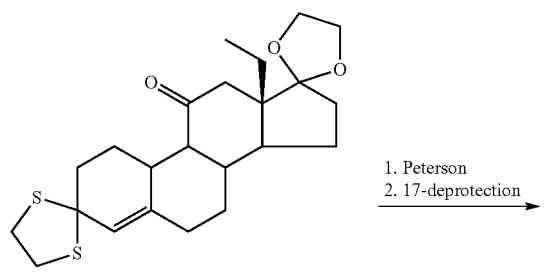

6
Molecular Weight (Da) = 420.63
Molecular Formula = C$_{23}$H$_{32}$O$_3$S$_2$

1. Peterson
2. 17-deprotection

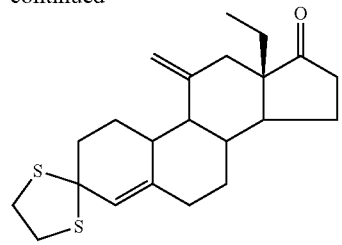

8
Molecular Weight (Da) = 374.61
Molecular Formula = C$_{22}$H$_{30}$OS$_2$

A suspension of magnesium (23.8 g, 980 mmol), iodine (50 mg, 0.20 mmol), chloromethyl trimethylsilane (2.9 g, 23.6 mmol) and dibromo ethane (1.7 g, 11 mmol) was reacted at 25° C. (temperature rise to 35° C.). The temperature was increased to 50° C. and a mixture of chloromethyl trimethylsilane (113 g, 1000 mmol) and dibromo ethane (1.7 g, 11 mmol) in THF (195 mL) and toluene (350 mL) was added in 60 min. The reagent mixture was brought to reflux temperature and a solution of steroid (6) (124 g, 294 mmol) in toluene (325 mL) was added in 1 h. After refluxing for 3 h, THF (200 mL) was distilled off. After another 5 h at reflux temperature the reaction was quenched with an ammonium chloride solution in water (160 g in 750 mL water), while maintaining the temperature below 25° C. Salts were removed via a filtration over dicalite. The layers were separated and the aqueous layer was extracted with toluene (two portions of 300 mL). The combined organic layers were washed with water (three portions of 400 mL). After a solvent switch to methanol (900 mL) a mixture of 36% aqueous HCl (31 g) and methanol (120 mL) was added. After reaction at 40° C. for 30 min, the reaction was quenched with an aqueous NaHCO$_3$ solution (41 g in 500 mL). The crystals were filtered off, washed with water and dried in vacuo. Product (8) yield: 95.7 g (255 mmol, 87%).

$^1$H NMR (600 MHz, CDCl$_3$): 0.76 (t, 3 H, C18H$_2$CH$_3$), 1.03 (m, 1 H, C7HH), 1.28 (m, 1 H, C18HHCH$_3$), 1.39 (m, 1 H, C9H), 1.43 (m, 1 H, C1HH), 1.45 (m, 1 H, C8H), 1.56 (m, 1 H, C18HHCH$_3$), 1.61 (m, 1 H, C14H), 1.65 (m, 1 H, C15HH), 1.80 (m, 1 H, C7HH), 1.83 (m, 1 H, C12HH), 1.91 (m, 1 H, C15HH), 1.98 (m, 1 H, C6HH), 2.06 (m, 1 H, C2HH), 2.12 (m, 1 H, C16HH), 2.19 (m, 1 H, C2HH), 2.28 (m, 1 H, C6HH), 2.27 (m, 1 H, C10H), 2.31 (m, 1 H, C1HH), 2.42 (m, 1 H, C16HH), 2.58 (m, 1 H, C12HH), 3.25 (m, 2 H, SCH$_2$CH$_2$S), 3.36 (m, 2 H, SCH$_2$CH$_2$S), 4.82 (s, 1 H, C11=CHH), 4.94 (s, 1 H, C11=CHH), 5.67 (s, 1 H, C4H). $^{13}$C NMR (150 MHz, CDCl$_3$): 7.2 (C18H$_2$CH$_3$), 18.1 (C18H$_2$CH$_3$), 20.8 (C15), 28.6 (C1), 30.4 (C7), 34.7 (C6), 35.8 (C10), 36.1 (C16), 39.5 (C12), 39.7 and 40.0 (SCH$_2$CH$_2$S), 40.4 (C2), 41.3 (C8), 52.1 (C14), 52.9 (C13), 54.5 (C9), 65.7 (C3), 110.2 (C11=CH$_2$), 126.6 (C4), 141.0 (C5), 145.6 (C11), 218.7 (C17). MS (ESI) observed ions 375/392 (M+H/M+NH$_4$)$^+$ and 766/771 [2M+NH$_4$/2M+Na]$^+$.

Example 5

11-methylene-13β-ethyl-,cyclic 17-(1,2-ethanediyl acetal),cyclic 3-(1,2-ethanediyl dithioacetal)gon-4-ene-3,17-dione (7)

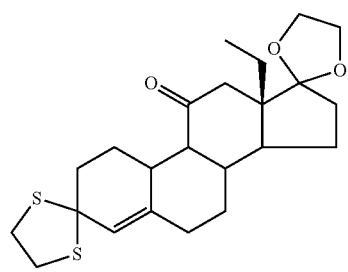

6
Molecular Weight (Da) = 420.63
Molecular Formula = C₂₃H₃₂O₃S₂

Wittig →

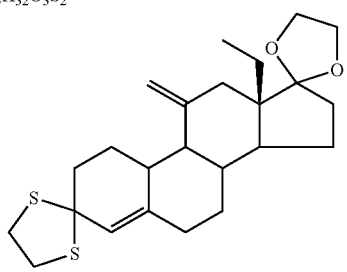

7
Molecular Weight (Da) = 418.66
Molecular Formula = C₂₄H₃₄O₂S₂

After formation of the reagent (reaction at reflux for 1 h with methyl trifenylfosfonium bromide (5.0 g, 14.1 mmol) and potassium tert-butoxide (1.47 g, 13.0 mmol) in toluene (38 mL)), a pre-dried solution of the steroid (6) (2.0 g, 4.75 mmol) in toluene (30 mL, water content 0.02%) was added. The reaction was continued at 90° C. for 2 days. Water (60 mL) was added and the layers were separated. The organic layer was washed with water (50 mL). Toluene was replaced by ethanol (50 mL). The crystals were filtered off, washed with ethanol and dried in vacuo. Product yield: 1.35 g (3.22 mmol, 68%). ¹H NMR (600 MHz, CDCl₃): 0.97 (m, 1 H, C7HH), 1.01 (t, 3 H, C18H₂CH₃), 1.28 (m, 1 H, C15HH), 1.31 (m, 1 H, C18HHCH₃), 1.32 (m, 1 H, C8H), 1.41 (m, 1 H, C9H), 1.41 (m, 1 H, C18HHCH₃), 1.42 (m, 1 H, C1HH), 1.60 (m, 1 H, C15HH), 1.70 (m, 1 H, C7HH), 1.75 (m, 1 H, C14H), 1.82 (m, 1 H, C16HH), 1.94 (m, 1 H, C6HH), 2.05 (m, 1 H, C2HH), 2.08 (m, 1 H, C16HH), 2.13 (m, 1 H, C12HH), 2.19 (m, 1 H, C2HH), 2.22 (m, 1 H, C6HH), 2.23 (m, 1 H, C10H), 2.30 (m, 1 H, C1HH), 2.37 (m, 1 H, C12HH), 3.24 (m, 2 H, SCH₂CH₂S), 3.36 (m, 2 H, SCH₂CH₂S), 3.84 (m, 2 H, OCH₂CH₂O), 3.90 (m, 2 H, OCH₂CH₂O), 4.72 (s, 1 H, C11=CHH), 4.93 (s, 1 H, C11=CHH), 5.64 (s, 1 H, C4H). ¹³C NMR (150 MHz, CDCl₃): 8.3 (C18H₂CH₃), 20.7 (C18H₂CH₃), 21.3 (C15), 28.6 (C1), 31.0 (C7), 34.8 (C16), 35.0 (C6), 35.9 (C10), 38.6 (C12), 39.6 and 40.0 (SCH₂CH₂S), 40.5 (C2), 42.0 (C8), 49.8 (C13), 51.9 (C14), 54.4 (C9), 64.3 and 65.3 (OCH₂CH₂O), 65.4 (C3), 108.4 (C11=CH₂), 119.8 (C17), 126.2 (C4), 141.7 (C5), 147.4 (C11). MS (ESI) observed ions 419 (M+H)⁺, 441 (M+Na)⁺, 854 (2M+NH₄)⁺.

Example 6

11-methylene-13β-ethyl-,cyclic 3-(1,2-ethanediyl dithioacetal)gon-4-ene-3,17-dione (8)

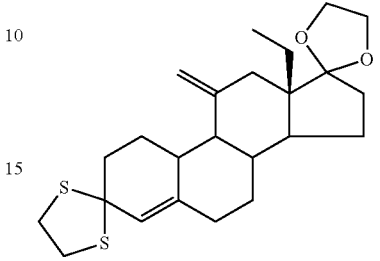

7
Molecular Weight (Da) = 418.66
Molecular Formula = C₂₄H₃₄O₂S₂

Deprotection →

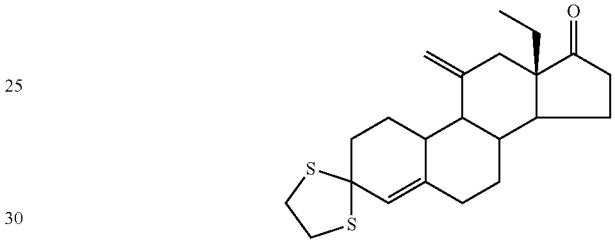

8
Molecular Weight (Da) = 374.61
Molecular Formula = C₂₂H₃₀OS₂

A solution of steroid (7) (1.1 g, 2.6 mmol) and 0.2 mL 96% sulfuric acid in water (0.5 mL) and acetone (4 mL) was stirred for 1.5 h at 20° C. The product was precipitated by the addition of water (36 mL) and a solution of NaOAc (1.2 g) in water (3.6 mL) at 20° C. The product (8) was isolated by filtration, washed with water and dried in vacuo. Product yield: 0.81 g (2.2 mmol, 83%). Spectral data were in agreement with data of Example 5.

Example 7

13β-ethyl-17α-hydroxy-11-methylene-, cyclic 1,2-ethanediyl dithioacetal-18,19-dinorpregn-4-en-20-yn-3-one (9)

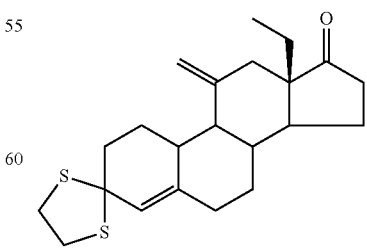

8
Molecular Weight (Da) = 374.61
Molecular Formula = C₂₂H₃₀OS₂

Ethynylation →

-continued

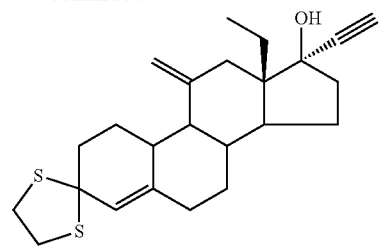

9
Molecular Weight (Da) = 400.65
Molecular Formula = C$_{24}$H$_{32}$OS$_2$

A solution of KOtBu (19.5 g, 174 mmol) in THF (200 mL) was saturated with acetylene at −10° C. To this potassium acetylide solution, a solution of steroid (8) (15 g, 40 mmol) and tBuOH (3 mL) in THF (130 mL) was added in 1 h at −10° C. After a reaction time of 2 h, a mixture of THF (20 mL) and acetic acid (20 mL) was added. Water (100 mL) was added and the layers were separated. The organic layer was concentrated in vacuo. The residue was dried by dissolving it in toluene and concentration in vacuo. Product yield: 15.5 g (38.7 mmol, 97%). $^1$H NMR (600 MHz, CDCl$_3$): 0.99 (m, 1 H, C7HH), 1.04 (t, 3 H, C18H$_2$CH$_3$), 1.34 (m, 1 H, C8H), 1.35 (m, 1 H, C15HH), 1.38 (m, 1 H, C9H), 1.42 (m, 1 H, C1HH), 1.43 (m, 2 H, C18H$_2$CH$_3$), 1.63 (m, 1 H, C15HH), 1.69 (m, 1 H, C7HH), 1.78 (m, 1 H, C14H), 1.96 (m, 1 H, C6HH), 2.06 (m, 1 H, C2HH), 2.10 (m, 1 H, C16HH), 2.21 (m, 1 H, C2HH), 2.23 (m, 1 H, C6HH), 2.24 (m, 1 H, C10H), 2.27 (m, 1 H, C12HH), 2.33 (m, 1 H, C1HH), 2.34 (m, 1 H, C16HH), 2.61 (m, 1 H, C12HH), 2.63 (s, 1 H, C17C≡CH), 3.25 (m, 2 H, SCH$_2$CH$_2$S), 3.37 (m, 2 H, SCH$_2$CH$_2$S), 4.77 (s, 1 H, C11=CHH), 4.99 (s, 1 H, C11=CHH), 5.65 (s, 1 H, C4H). $^{13}$C NMR (150 MHz, CDCl$_3$): 9.1 (C18H$_2$CH$_3$), 19.8 (C18H$_2$CH$_3$), 21.9 (C15), 28.6 (C1), 31.1 (C7), 35.0 (C6), 35.9 (C10), 39.7 (C16), 40.5 (C12), 39.8 and 40.0 (SCH$_2$CH$_2$S), 40.5 (C2), 42.3 (C8), 50.4 (C13), 52.2 (C14), 54.1 (C9), 65.8 (C3), 74.2 and 87.7 (C17C≡CH), 81.06 (C17), 108.7 (C11=CH$_2$), 126.3 (C4), 141.5 (C5), 147.0 (C11). MS (ESI) observed ions 401/419/423=[M+H/M+NH$_4$/M+Na]$^+$ Example 8

Preparation of Etonogestrel

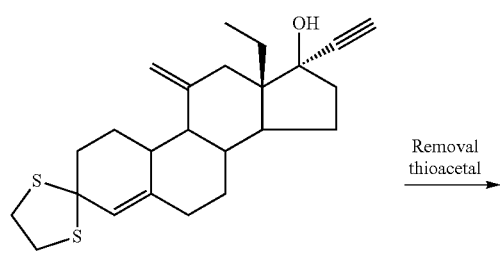

9
Molecular Weight (Da) = 400.65
Molecular Formula = C$_{24}$H$_{32}$OS$_2$

Removal thioacetal

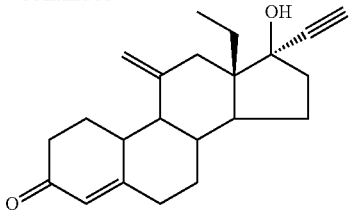

Etonogestrel
Molecular Weight (Da) = 324.46
Molecular Formula = C$_{22}$H$_{28}$O$_2$ Example 8A Thioacetal Removal Using Periodic Acid To a solution of steroid (9) (4.0 g, 10 mmol) in dichloro methane (25 mL) a solution of periodic acid (0.85 g, 3.7 mmol) in methanol/water 1:1 (10 mL) was added at 2° C. After a complete conversion, the reaction was quenched by a solution of NaOH (0.4 g) in water (10 mL). The pH was brought to ca 7 by the addition of 3.6% aqueous HCl (2.6 mL). The layers were separated and the product was extracted with dichloromethane. The combined organic layers were concentrated in vacuo. The residue was purified by column chromatography over silica gel (eluent dichloro methane). Product yield: 2.8 g (9.0 mmol, 90%). Identity of etonogestrel ($^1$H NMR, TLC, and HPLC) was confirmed by comparison with a sample of etonogestrel.

Example 8B

Thioacetal Removal Using Thallium Nitrate

A solution of thallium nitrate (6.7 g, 15 mmol) in methanol (50 mL) was added to a solution of steroid (9) (3.99 g, 10 mmol) in a mixture of methanol (50 mL), THF (50 mL) and water (25 mL) at 2° C. After a reaction time of 2.5 h, a solution of sodium hydroxide (1 g) in water (25 mL) was added. The layers were separated, concentrated in vacuo and a silica filtration was carried out with dichloro methane as eluent. The residue thus obtained following concentration was taken up in dichloro methane (50 mL) and the organic layer was washed with water (3×50 mL). The product was obtained as a solid after concentration of the organic layer. Product yield: 3.17 g (9.8 mmol, 98%). Identity of etonogestrel ($^1$H NMR, TLC, and HPLC) was confirmed by comparison with a sample of etonogestrel.

Example 8C

Thioacetal Removal Using Stabilized 2-Iodoxybenzoic Acid

A solution of steroid (9) (3.90 g, 10 mmol), 5.7 g stabilized 2-iodoxybenzoic acid (SIBX, 20 mmol) and β-cyclodextrine (2.3 g, 2.0 mmol) in methanol (100 mL) and water (20 mL) was stirred for 17 h at room temperature. A solution of sodium hydroxide (1 g) in water (25 mL) was added. The layers were separated, concentrated in vacuo and a silica filtration was carried out with dichloro methane as eluent. The thus obtained concentrated residue was taken up in dichloro methane (50 mL) and the organic layer was washed with water (3×50 mL). The product was obtained as a solid after concentration of the organic layer. Product yield: 4.5 g (>100% caused by reagent remainders). Identity of etonogestrel ($^1$H NMR, TLC, and HPLC) was confirmed by comparison with a sample of etonogestrel.

Example 9

Preparation of Desogestrel

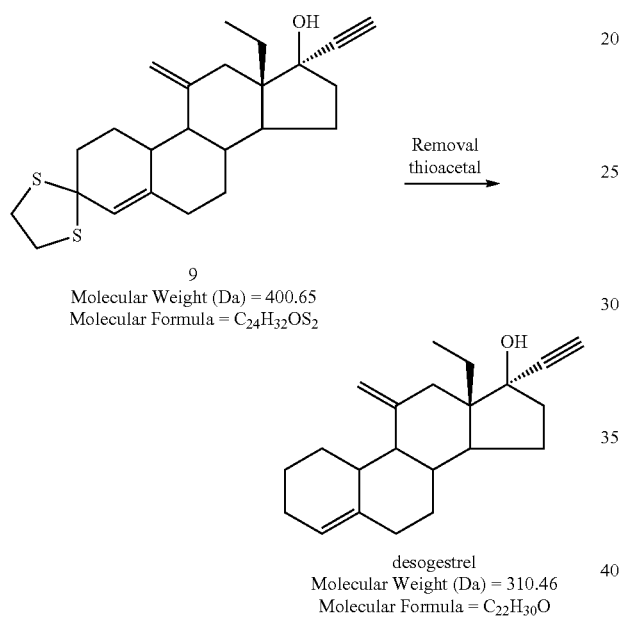

A solution of sodium (3.86 g, 168 mmol) and copper nitrate (0.8 mg, 4.3 µmol) in ammonia (110 mL) was agitated for 1 h at −36° C. A solution of steroid 9 (10.8 g, 26.7 mmol) was added to the ammonia solution. After stirring for 45 min at −36° C., the reaction was quenched by the addition of CH$_3$CN (4 mL). The ammonia was evaporated till an internal temperature of −14° C. A mixture of THF (9.5 mL) and water (0.5 mL) was added and the temperature was allowed to further increase to 0° C. When all ammonia was evaporated, water was added (75 mL). The reaction mixture was stirred overnight at ambient temperature, 2.5 h at 30° C., cooled to 0° C. and neutralized to pH 7 with a 25% aqueous sulfuric acid solution. The reaction mixture was distilled free of solvents in vacuo. After two co-evaporation steps with acetone, the solid material was isolated by filtration, washed and dried at 30° C. in vacuo. The product was obtained in a quantitative yield. Identity of desogestrel CH NMR, TLC, HPLC) was confirmed by comparison with a sample of desogestrel.

The invention claimed is:
1. A process for the manufacture of a steroid derivative according to general formula IX

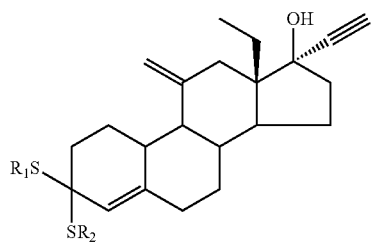

using a steroid derivative of general formula VI or VII

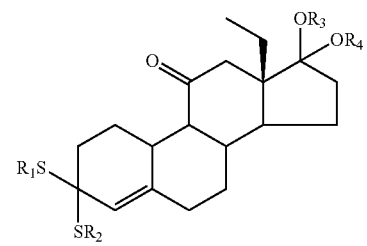

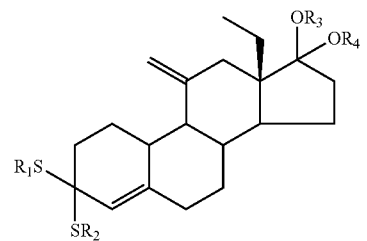

wherein in the steroid derivatives of general formula VI, VII and IX, $R_1$ and $R_2$ are the same and are selected from H and (1-4C)alkyl; or $R_1$ and $R_2$, together with the sulphur atoms to which they are attached, form a 1,3-dithiolane or 1,3-dithiane, said dithiolane or dithiane being optionally substituted with one or more (1-4C)alkyl group; and $R_3$ and $R_4$ are the same and are selected from H and (1-4C)alkyl; or $R_3$ and $R_4$, together with the oxygen atoms to which they are attached, form a 1,3-dioxolane or 1,3-dioxane, said dioxolane or dioxane being optionally substituted with one or more (1-4C)alkyl group.

2. The process according to claim 1 comprising steps 1 through 6 according to the following scheme:

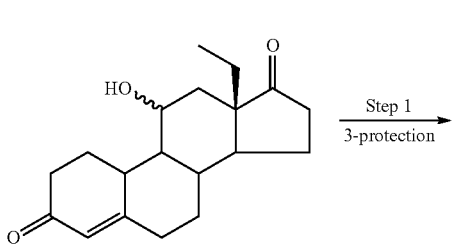

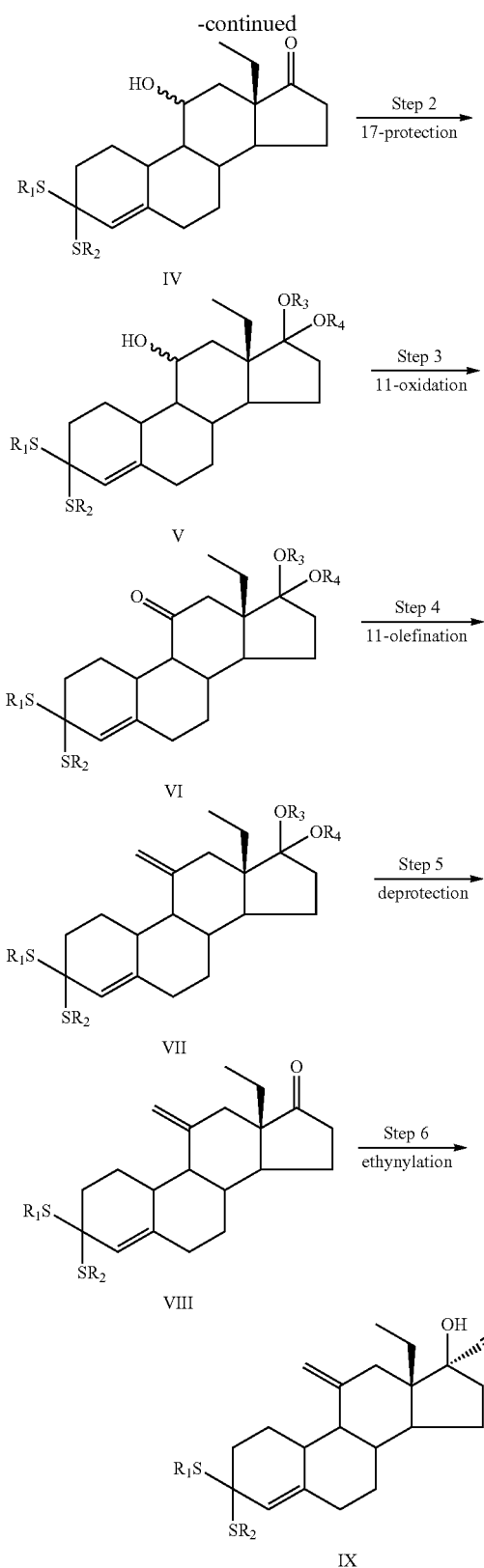

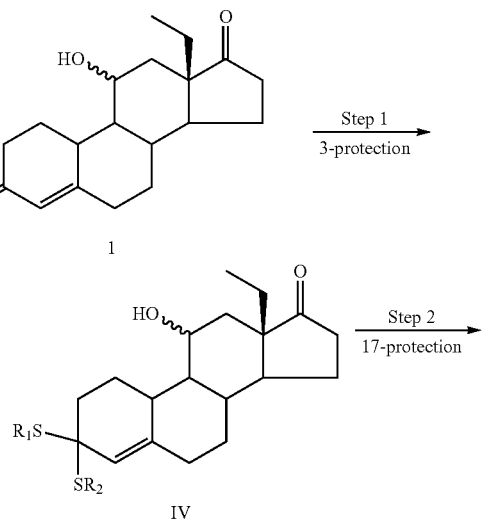

sulphur atoms to which they are attached, form a 1,3-dithiolane or 1,3-dithiane, said dithiolane or dithiane being optionally substituted with one or more (1-4C)alkyl group and in the steroid derivatives of general formula V, VI and VII, $R_3$ and $R_4$ are the same and are selected from H and (1-4C)alkyl; or $R_3$ and $R_4$, together with the oxygen atoms to which they are attached, form a 1,3-dioxolane or 1,3-dioxane, said dioxolane or dioxane being optionally substituted with one or more (1-4C)alkyl group, wherein in step 1, 13β-ethyl-11-hydroxygon-4-ene-3,17-dione, (1) is reacted with a thioalcohol or dithioalcohol into a 3-dithioacetal steroid derivative of general formula IV;

in step 2, the 3-dithioacetal steroid derivative of general formula IV is reacted with an alcohol or diol to obtain a 17-acetal,-3-dithioacetal steroid derivative of general formula V;

in step 3, the 11-hydroxy group in the 17-acetal-3-dithioacetal steroid derivative of general formula V is oxidized to obtain a 11-keto-17-acetal-3-dithioacetal steroid derivative of general formula VI;

in step 4, the 11-keto-17-acetal-3-dithioacetal steroid derivative of general formula VI is methylenylated to give a 11-methylene-17-acetal-3-dithioacetal steroid derivative of general formula VII;

in step 5, the 11-methylene-17-acetal-3-dithioacetal steroid derivative of general formula VII is hydrolysed to obtain a 11-methylene 3-dithioacetal steroid derivative of general formula VIII and in step 6, the 11-methylene 3-dithioacetal steroid derivative of general formula VIII is ethynylated to give a 20-yn-11-methylene-3-dithioacetal steroid derivative of general formula IX.

3. The process according claim 2, wherein in step 4, the 11-keto group is converted into a methylene group using Peterson reaction conditions and the 11-methylene 17-acetal, 3-dithioacetal steroid derivative of general formula VII is reacted without isolation.

4. The process according to claim 2, wherein in step 4, the 11-keto group is converted into a 11-methylene group using Wittig reaction conditions.

5. A process for the manufacture of etonogestrel comprising steps 1 through 7, wherein etonogestrel is obtained from the 20-yn-11-methylene-3-dithioacetal steroid derivative of general formula IX by deprotection of the 3-dithioactetal wherein, in the steroid derivatives of general formula IV, V, VI, VII, VIII and IX, $R_1$ and $R_2$ are the same and are selected from H and (1-4C)alkyl; or $R_1$ and $R_2$, together with the

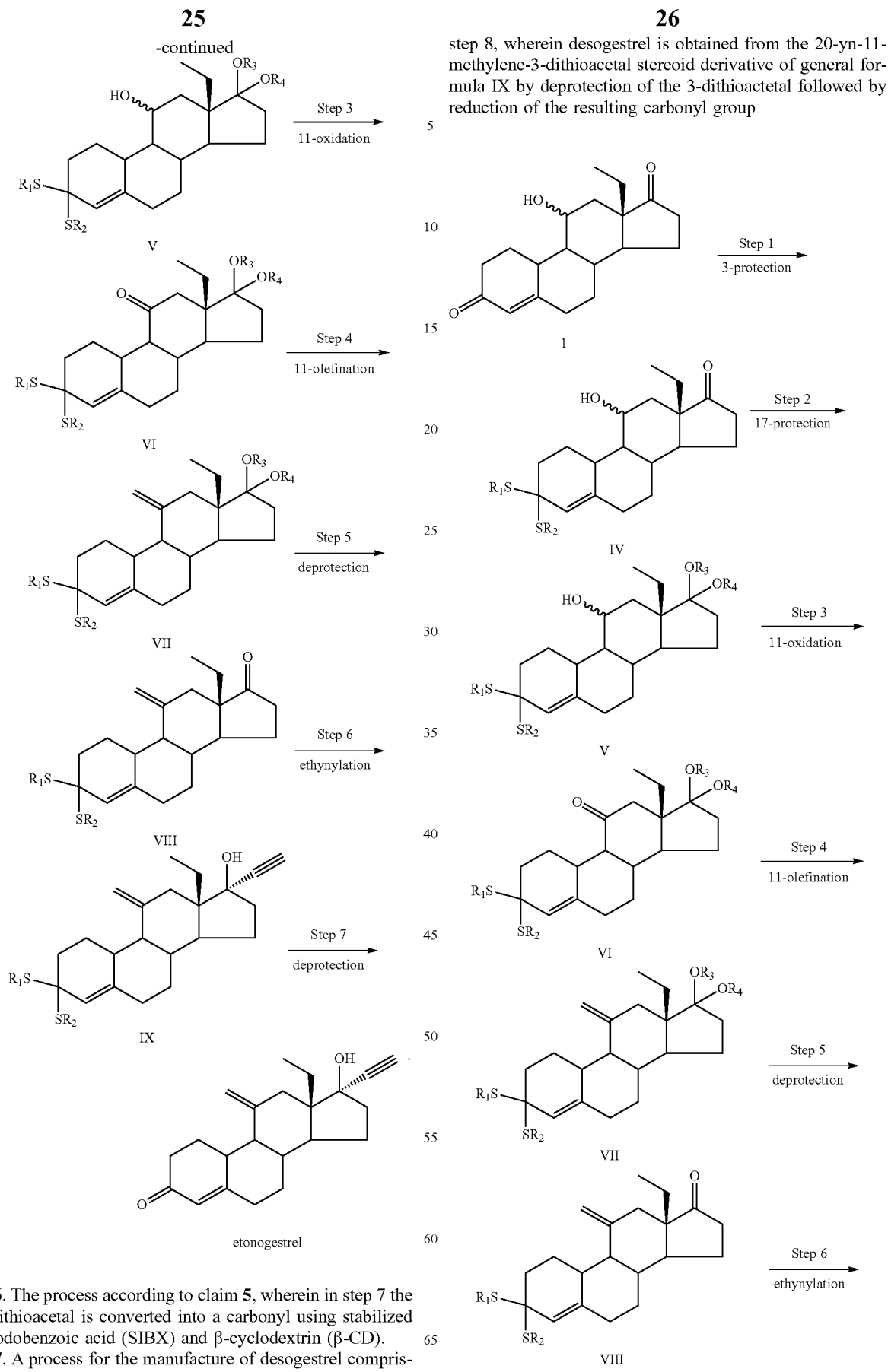

step 8, wherein desogestrel is obtained from the 20-yn-11-methylene-3-dithioacetal steroid derivative of general formula IX by deprotection of the 3-dithioacetal followed by reduction of the resulting carbonyl group

6. The process according to claim 5, wherein in step 7 the 3-dithioacetal is converted into a carbonyl using stabilized 2-iodobenzoic acid (SIBX) and β-cyclodextrin (β-CD).

7. A process for the manufacture of desogestrel comprising steps 1 through 6 and further comprising an additional

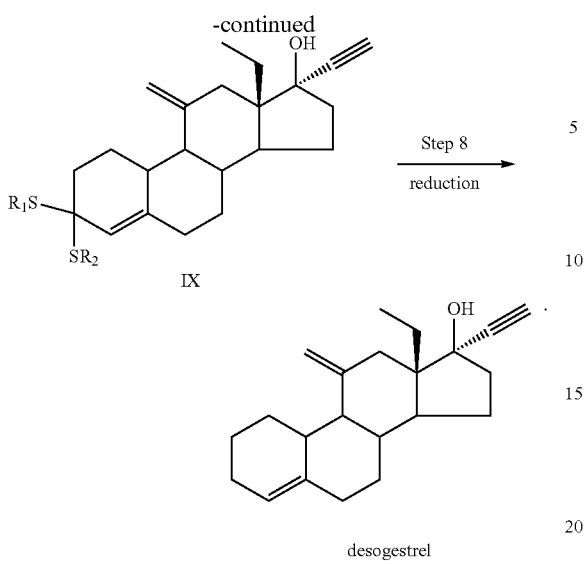

desogestrel

8. The process according to claim 5, wherein
$R_1$ and $R_2$, together with the sulphur atoms to which they are attached, form a 1,3-dithiolane;
$R_3$ and $R_4$, together with the oxygen atoms to which they are attached, form a 1,3-dioxolane;
in step 3, the 11-hydroxy group in the 17-acetal,-3-dithioacetal steroid derivative of general formula V is oxidised using pyridinium dichromate;
in step 4, the 11-keto-17-acetal-3-dithioacetal steroid derivative of general formula VI is methylenylated using Peterson reaction conditions followed by deprotection of the 17-diacetal (step 5) using hydrochloric acid without isolation of the 11-methylene-17-acetal-3-dithioacetal steroid derivative of general formula VII and
in step 7, the 3-dithioacetal is deprotected using periodic acid.

9. The process according to claim 7, wherein
$R_1$ and $R_2$, together with the sulphur atoms to which they are attached, form a 1,3-dithiolane;
$R_3$ and $R_4$, together with the oxygen atoms to which they are attached, form a 1,3-dioxolane;
in step 3, the 11-hydroxy group in the 17-acetal,-3-dithioacetal steroid derivative of general formula V is oxidised using pyridinium dichromate;
in step 4, the 11-keto-17-acetal-3-dithioacetal steroid derivative of general formula VI is methylenylated using Peterson reaction conditions followed by deprotection of the 17-diacetal (step 5) using hydrochloric acid without isolation of the 11-methylene-17-acetal-3-dithioacetal steroid derivative of general formula VII; and
in step 7, the 3-dithioacetal is deprotected using periodic acid.

10. A steroid derivative of general formula VI or VII,

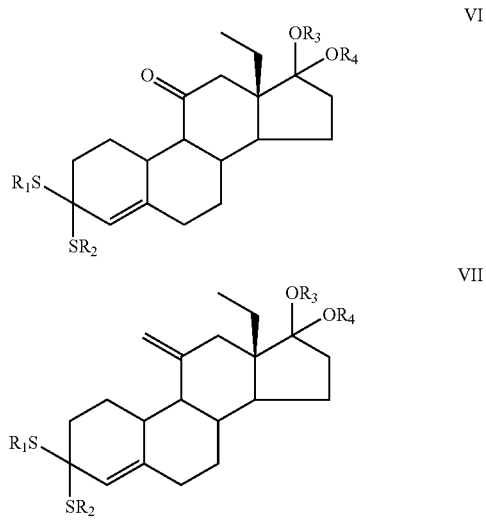

wherein,
$R_1$ and $R_2$ are the same and are selected from H and (1-4C)alkyl; or $R_1$ and $R_2$, together with the sulphur atoms to which they are attached, form a 1,3-dithiolane or 1,3-dithiane, said dithiolane or dithiane being optionally substituted with one or more (1-4C)alkyl group and $R_3$ and $R_4$ are the same and are selected from H and (1-4C)alkyl; or $R_3$ and $R_4$, together with the oxygen atoms to which they are attached, form a 1,3-dioxolane or 1,3-dioxane, said dioxolane or dioxane being optionally substituted with one or more (1-4C)alkyl group.

11. The steroid derivative according to claim 10 selected from:
13β-ethyl-cyclic-3-(1,2-ethanediyl dithioacetal)-cyclic-17-(1,2-ethanediyl acetal)-gon-4-ene-3,11,17-trione (6); and
13β-ethyl-11-methylene-cyclic-3-(1,2-ethanediyl dithioacetal)-cyclic-17-(1,2-ethanediyl acetal)-gon-4-ene-3,17-dione (7).

* * * * *